US008920832B2

United States Patent
Kikuchi et al.

(10) Patent No.: US 8,920,832 B2
(45) Date of Patent: Dec. 30, 2014

(54) COMPOSITION FOR NUCLEIC ACID TRANSFECTION

(75) Inventors: Hiroshi Kikuchi, Koto-ku (JP); Hideo Kobayashi, Edogawa-ku (JP); Kouichi Hashimoto, Yachiyo (JP); Ayako Iijima, Fukuyama (JP); Daigo Asano, Koto-ku (JP); Junko Yasuda, Takaoka (JP)

(73) Assignee: Hokkaido System Science Co., Ltd., Sapporo-shi (JP)

( * ) Notice: Subject to any disclaimer, the term of this patent is extended or adjusted under 35 U.S.C. 154(b) by 414 days.

(21) Appl. No.: 13/249,120

(22) Filed: Sep. 29, 2011

(65) Prior Publication Data
US 2013/0149369 A1 Jun. 13, 2013

Related U.S. Application Data

(63) Continuation of application No. 12/306,993, filed as application No. PCT/JP2007/000719 on Jun. 29, 2007, now abandoned.

(30) Foreign Application Priority Data

Jun. 30, 2006 (JP) .................................. 2006-181642

(51) Int. Cl.
*A61K 31/7088* (2006.01)
*A61K 48/00* (2006.01)

(52) U.S. Cl.
CPC ......... *A61K 31/7088* (2013.01); *A61K 48/0025* (2013.01)
USPC .......... 424/450; 435/458; 435/6.13; 435/375; 514/44 R; 514/44 A

(58) Field of Classification Search
None
See application file for complete search history.

(56) References Cited

U.S. PATENT DOCUMENTS

2005/0175683 A1* 8/2005 Zhang ........................... 424/450

OTHER PUBLICATIONS

Zeisig et al (Cancer Gene Therapy. 2003; 10:302-311).*
Feitosa et al (Chemistry and Physics of Lipids. 2006; 142: 128-132).*
Sun et al. (Journal of Drug Targeting. 2005; 13(2): 121-128).*

* cited by examiner

*Primary Examiner* — Scott Long
(74) *Attorney, Agent, or Firm* — Oblon, Spivak, McClelland, Maier & Neustadt, L.L.P.

(57) ABSTRACT

The invention provides a nucleic-acid-transfecting composition which exhibits low cytotoxicity, which facilitates an effective nucleic acid transfection into a cell, and which improves expression of the nucleic acid in the cell.
The composition for transfecting a nucleic acid into a cell, contains a di($C_{12-16}$ alkyl)dimethylammonium halide and a phospholipid.

12 Claims, No Drawings

US 8,920,832 B2

COMPOSITION FOR NUCLEIC ACID TRANSFECTION

CROSS REFERENCE TO RELATED APPLICATIONS

The present application is a continuing application of U.S. application Ser. No. 12/306,993, filed Dec. 30, 2008, which is the national stage of international application PCT/JP2007/00719, filed on Jun. 29, 2007, and claims the benefit of the filing date of Japanese Application No. 2006-181642, filed on Jun. 30, 2006, the text of each which is incorporated by reference.

TECHNICAL FIELD

The present invention relates to a composition for a nucleic acid transfection into cells (hereinafter may be referred to as a "nucleic-acid-transfecting composition").

BACKGROUND ART

For a nucleic acid (e.g., a gene) transfection into cells, there have already been known methods which make use of cationic lipid alone, or a complex formed between the nucleic acid and liposomes containing cationic lipid (see, for example, Patent Document 1). In such a method, commercially available reagents such as "Lipofectamine," "Lipofectin," "Transfectam," "Genetransfer," and "Lipofectamine 2000" are employed.

However, these commercially available reagents pose problems as described below. (a) Such a commercially available reagent exhibits poor storage stability, or fails to attain intracellular transfection and expression of a gene by use of, for example, liposomes at high reproducibility. (b) Such a commercially available reagent is very unstable in serum (fetal bovine serum) added to a medium for cell culture, and thus the reagent requires an intricate process for a nucleic acid transfection (i.e., a serum-containing medium in which cells are cultured is temporarily replaced with a serum-free medium, and then the serum-free medium is replaced with the serum-containing medium after a nucleic acid transfection). Recently, it has been become clear that such a commercially available reagent is very unstable also in blood or a living body. (c) Most of these commercially available reagents (e.g., Lipofectamine, Lipofectin, and Lipofectamine 2000) are provided only in the form of a dispersion containing lipid dispersed in water. Therefore, an aqueous solution of a gene is added to such a reagent for the gene transfection. However, in such a case, liposomes encapsulating the gene fail to be produced, although a complex in which the gene is bound to the outside of liposomes can be produced. Lipofectamine 2000 should not be excessively stirred or shaken and must be handled with the greatest care for preventing formation of cationic lipid peroxide. (d) Such a commercially available reagent exhibits very potent cytotoxicity.

Thus, many problems are involved in some commercially available reagents for a nucleic acid (e.g., a gene) transfection into cells by use of cationic lipid singly or cationic-lipid-containing liposomes.

Patent Document 1: JP-A-1990-135092

DISCLOSURE OF THE INVENTION

Problems to be Solved by the Invention

An object of the present invention is to provide a nucleic-acid-transfecting composition which exhibits low cytotoxicity, which facilitates an effective nucleic acid transfection into cells, and which improves expression of the nucleic acid in the cells.

Means for Solving the Problems

The present inventors have conducted extensive studies on means for achieving low cytotoxicity, facilitating an effective nucleic acid (e.g., a gene) transfection into cells, and improving expression of the nucleic acid in the cells, and as a result have found that when a di($C_{12-16}$ alkyl)dimethylammonium halide, a phospholipid, and a nucleic acid (e.g., a gene) are administered to a subject in need thereof or transfected into cells, problems associated with cytotoxicity do not arise, and the nucleic acid is effectively transfected into the cells. The present invention has been accomplished on the basis of this finding.

Accordingly, the present invention provides the following.

(1) A composition for transfecting a nucleic acid into a cell, comprising a di($C_{12-16}$ alkyl)dimethylammonium halide and a phospholipid.

(2) A composition for transfecting a nucleic acid into a cell, comprising ditetradecyldimethylammonium bromide, dioleoylphosphatidylethanolamine, and cholesterol.

(3) A composition for transfecting a nucleic acid into a cell, comprising ditetradecyldimethylammonium bromide, dioleoylphosphatidylethanolamine, cholesterol, and protamine.

(4) A method for transfecting a nucleic acid into a cell, comprising applying, to a cell in vitro or in vivo, a composition comprising a di($C_{12-16}$ alkyl)dimethylammonium halide, a phospholipid, and a nucleic acid.

(5) Use of a composition as recited in any one of 1) to 3) for producing a nucleic-acid-transfecting agent.

(6) A screening method for selecting a substance which inhibits expression of a target nucleic acid, comprising the following steps (i) to (iii):

(i) a step of bringing a test substance into contact with a cell into which a target nucleic acid has been transfected;

(ii) a step of determining the level of expression of the target nucleic acid in the cell which has been brought into contact with the test substance; and (iii) a step of selecting a test substance showing an expression level as determined in (ii) above that is lower than the level of expression of the target nucleic acid in a control cell, wherein transfection of the target nucleic acid into the cell and/or exposure of the cell to the test substance is carried out by use of a composition as recited in any one of (1) to (3).

Effects of the Invention

The composition of the present invention poses no cytotoxicity-associated problems and realizes an effective nucleic acid transfection into cells. Therefore, the composition of the present invention is useful as a nucleic-acid-transfecting reagent or drug.

BEST MODES FOR CARRYING OUT THE INVENTION

The nucleic-acid-transfecting composition of the present invention is employed together with a nucleic acid which is to be transfected into cells (hereinafter the nucleic acid may be referred to as a "nucleic acid of interest"). No particular limitation is imposed on the composition, so long as it contains at least a di($C_{12-16}$ alkyl)dimethylammonium halide and a phospholipid. The composition of the present invention includes a composition containing a nucleic acid of interest (i.e., a nucleic-acid-containing composition) and a composition containing no nucleic acid of interest.

The di($C_{12-16}$ alkyl)dimethylammonium halide contained in the composition of the present invention is a known compound and may be produced through a known method. Each $C_{12-16}$ alkyl group bonded to the nitrogen atom of this compound is, for example, a dodecyl group, a tridecyl group, a tetradecyl group, a pentadecyl group, or a hexadecyl group, and the two $C_{12-16}$ alkyl groups bonded to the nitrogen atom may be identical to or different from each other. Examples of the halide include a chloride and a bromide. The di($C_{12-16}$ alkyl)dimethylammonium halide may be a commercially available product; for example, a product of Sogo Pharmaceutical Co., Ltd., such as didodecyldimethylammonium bromide (product name: DC-1-12), dimethylditetradecylammonium bromide (product name: DC-1-14), or dihexadecyldimethylammonium bromide (product name: DC-1-16). In the present invention, the di($C_{12-16}$ alkyl)dimethylammonium halide is particularly preferably dimethylditetradecylammonium bromide.

The amount of the di($C_{12-16}$ alkyl)dimethylammonium halide contained in the composition of the present invention may be appropriately determined on the basis of the total lipid content of the composition of the present invention. However, the amount of the di($C_{12-16}$ alkyl)dimethylammonium halide is preferably 20 to 60 mol %, more preferably 30 to 50 mol %, on the basis of the total lipid content of the composition.

Examples of the phospholipid contained in the composition of the present invention include phosphatidylethanolamine, phosphatidylcholine, phosphatidylserine, phosphatidylinositol, phosphatidylglycerol, cardiolipin, sphingomyelin, plasmalogen, and phosphatidic acid. These phospholipids may be employed singly or in combination of two or more species.

More preferably, phosphatidylethanolamine or phosphatidylcholine is employed singly, or these are employed in combination. Particularly preferably, phosphatidylethanolamine is employed. No particular limitation is imposed on the fatty acid group of such a phospholipid, and the fatty acid group may be a $C_{12-18}$ saturated or unsaturated fatty acid group. Examples of preferred fatty acid groups include a palmitoyl group, an oleoyl group, a stearoyl group, and a linoleyl group. The phospholipid employed in the present invention is particularly preferably dioleoylphosphatidylethanolamine.

The amount of the aforementioned phospholipid contained in the composition of the present invention may be appropriately determined on the basis of the total lipid content of the composition. However, the ratio by mole of the di($C_{12-18}$ alkyl)dimethylammonium halide to the phospholipid is preferably 1:4 to 4:1, more preferably 2:3 to 3:2.

The composition of the present invention may further contain a sterol compound (e.g., cholesterol and/or cholestanol). The amount of the sterol compound is preferably 0 to 50 mol %, more preferably 10 to 50 mol %, on the basis of the total lipid content of the composition.

The amount of the aforementioned phospholipid contained in the composition of the present invention may be appropriately determined on the basis of the total lipid content of the composition. However, the ratio by mole of the di($C_{12-18}$ alkyl)dimethylammonium halide to the phospholipid is preferably 1:4 to 4:1, more preferably 2:3 to 3:2.

No particular limitation is imposed on the nucleic acid of interest to which the composition of the present invention is applied, and the nucleic acid may be an oligonucleotide, DNA, or RNA. Examples of the nucleic acid include short oligonucleotides such as antisense oligonucleotide, antisense DNA, antisense RNA, shRNA, siRNA, and miRNA; bioactive substances such as enzyme and cytokine; and genes encoding antisense RNA, shRNA, and siRNA.

For more effective nucleic acid transfection into cells, the composition of the present invention may further contain a component known as an enhancer, such as poly L-lysine, protamine or a salt thereof, pronectin, spermine, a nuclear localization signal (NLS), or sodium butyrate. These enhancers may be employed singly or in combination.

No particular limitation is imposed on the amount of the di($C_{12-16}$ alkyl)dimethylammonium halide contained in the composition of the present invention, so long as the amount is enough to transfect a nucleic acid into cells. The amount of the di($C_{12-16}$ alkyl)dimethylammonium halide may be appropriately determined in consideration of, for example, the type of a nucleic acid of interest, the use of the nucleic acid, or the form of the composition. For example, in the case of a nucleic acid (200 ng) transfection, the amount of the di($C_{12-16}$ alkyl)dimethylammonium halide contained in the composition is preferably 125 to 2,000 µmol, more preferably 250 to 1,000 µmol. In the case of siRNA transfection, the amount of the di($C_{12-16}$ alkyl)dimethylammonium halide contained in the composition is preferably 0.1 to 10 mol, more preferably 0.5 to 2 mol against 1 mol of phosphate group. For example, in the case of 27-mer siRNA (1 mol) transfection, the amount of the di($C_{12-16}$ alkyl)dimethylammonium halide contained in the composition is preferably 5.4 to 540 mol, more preferably 27 to 108 mol.

The composition of the present invention may be in the form of a simple mixture of a di($C_{12-16}$ alkyl)dimethylammonium halide, a phospholipid, and an optional sterol compound or enhancer. Alternatively, the composition may be in the form of a lipid membrane structure produced from a di($C_{12-16}$ alkyl)dimethylammonium halide, a phospholipid, and a sterol compound.

No particular limitation is imposed on the form of the lipid membrane structure, and the lipid membrane structure may be in the form of, for example, a dried lipid mixture, an aqueous solvent dispersion, or a dried or frozen product of the dispersion.

Examples of the aqueous solvent dispersion form of the lipid membrane structure include a single-lamellar liposome, a multi-lamellar liposome, an O/W emulsion, a W/O/W emulsion, a spherical micelle, a thread-like micelle, and an amorphous layered structure. Of these, a liposome form is preferred. No particular limitation is imposed on the size of the dispersed lipid membrane structure. For example, when the lipid membrane structure is in the form of liposomes or emulsion, the structure has a particle size of 50 nm to 5 µm, whereas when the lipid membrane structure is in the form of spherical micelles, the structure has a particle size of 5 to 100 nm. When the lipid membrane structure is in the form of thread-like micelles or amorphous layered structure, the structure is preferably lamellar forms each having a thickness of 5 to 10 nm.

Next will be described methods for producing various forms of the lipid membrane structure.

(1) The lipid membrane structure in the form of dried mixture may be produced by, for example, temporarily dissolving all the components of the lipid membrane structure in an organic solvent (e.g., chloroform), and then subjecting the resultant solution to drying under reduced pressure by means of an evaporator, or to spray drying by means of a spray dryer.

(2) The lipid membrane structure in the form of aqueous solvent dispersion may be produced by adding the aforementioned dried mixture to an aqueous solvent, and then emulsifying the resultant mixture by means of, for example, an emulsifier (e.g., a homogenizer), an ultrasonic emulsifier, or a high-pressure jet emulsifier. Alternatively, the lipid membrane structure in the form of aqueous solvent dispersion may be produced through a method well-known as a liposome production method (e.g., the reverse-phase evaporation method). For control of the size of the lipid membrane structure, extrusion (extrusion typed filtration) may be carried out under high pressure by means of, for example, a membrane filter having pores of uniform size.

No particular limitation is imposed on the composition of an aqueous solvent (dispersion medium) employed. Examples of the aqueous solvent which may be employed include buffers such as phosphate buffer, citrate buffer, and phosphate buffered saline; saline; and culture media for cell culture. Such an aqueous solvent (dispersion medium), in which the lipid membrane structure can be stably dispersed, may further contain, for example, a sugar (or an aqueous solution thereof), or a polyhydric alcohol (or an aqueous solution thereof). Examples of the sugar include monosaccharides such as glucose, galactose, mannose, fructose, inositol, ribose, and xylose; disaccharides such as lactose, sucrose, cellobiose, trehalose, and maltose; trisaccharides such as raffinose and melezitose; polysaccharides such as cyclodextrin; and sugar alcohols such as erythritol, xylitol, sorbitol, mannitol, and maltitol. Examples of the polyhydric alcohol include glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, and 1,3-butylene glycol. In order to stably store the lipid membrane structure dispersed in such an aqueous solvent (dispersion medium) for a long period of time, preferably, the amount of electrolytes in the aqueous solvent (dispersion medium) is reduced to a minimum possible level, from the viewpoint of physical stability (e.g., from the viewpoint of preventing aggregation). From the viewpoint of chemical stability of lipid, preferably, the pH of the aqueous solvent (dispersion medium) is adjusted to fall within a range of 3.0 to 8.0 (i.e., from slightly acidic to around neutral), or dissolved oxygen is removed through nitrogen bubbling.

No particular limitation is imposed on the sugar or polyhydric alcohol concentration of the aqueous solvent in which the lipid membrane structure is dispersed. However, for example, the sugar (or aqueous solution thereof) concentration is preferably 2 to 20% (w/v), more preferably 5 to 10% (w/v), and the polyhydric alcohol (or aqueous solution thereof) concentration is preferably 1 to 5% (w/v), more preferably 2 to 2.5% (w/v). When the aqueous solvent (dispersion medium) employed is a buffer, the buffering agent concentration of the buffer is preferably 5 to 50 mM, more preferably 10 to 20 mM. No particular limitation is imposed on the lipid membrane structure concentration of the aqueous solvent dispersion, but the total lipid concentration (the amounts of components of the lipid membrane structure, including $di(C_{12-16}$ alkyl)dimethylammonium halide, phospholipid, and optional sterol compound) of the dispersion is preferably 0.2 to 50 mM, more preferably 1 to 10 mM.

(3) A dried or frozen product of the lipid membrane structure dispersed in any of the aforementioned aqueous solvents may be produced by subjecting the aqueous solvent dispersion of the lipid membrane structure to a common drying process (e.g., lyophilization or spray drying) or to a freezing process. When the above-produced aqueous solvent dispersion of the lipid membrane structure is further dried, the lipid membrane structure can be stored for a long period of time. When an aqueous solution containing a nucleic acid is added to the thus-dried lipid membrane structure, advantageously, the lipid mixture is effectively hydrated, and thus the nucleic acid can be effectively retained in the lipid membrane structure.

In the case where the aqueous solvent dispersion of the lipid membrane structure is lyophilized or spray-dried, when a sugar (e.g., a monosaccharide such as glucose, galactose, mannose, fructose, inositol, ribose, or xylose; a disaccharide such as lactose, sucrose, cellobiose, trehalose, or maltose; a trisaccharide such as raffinose or melezitose; a polysaccharide such as cyclodextrin; or a sugar alcohol such as erythritol, xylitol, sorbitol, mannitol, or maltitol) or an aqueous solution thereof is employed, the lipid membrane structure can be stably stored for a long period of time. In the case where the aqueous solvent dispersion of the lipid membrane structure is frozen, when any of the aforementioned sugars (or an aqueous solution thereof), or a polyhydric alcohol (e.g., glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, or 1,3-butylene glycol) or an aqueous solution thereof is employed, the lipid membrane structure can be stably stored for a long period of time. Such a sugar and polyhydric alcohol may be employed in combination.

The nucleic-acid-transfecting composition of the present invention may be in the form of a composition containing a nucleic acid of interest (i.e., a nucleic-acid-containing composition). Such a nucleic-acid-containing composition will next be described.

The nucleic-acid-containing composition may be in the form of a simple mixture of a $di(C_{12-16}$ alkyl)dimethylammonium halide, a phospholipid, a nucleic acid, and an optional sterol compound or enhancer. Alternatively, the composition may be in the form of a mixture of a nucleic acid and a lipid membrane structure formed of a $di(C_{12-16}$ alkyl)dimethylammonium halide, a phospholipid, and a sterol compound. The lipid membrane structure may retain the nucleic acid. As used herein, the term "retain" refers to the case where nucleic acid is present in a lipid membrane of the lipid membrane structure, on the surface of the membrane, inside of the membrane, in a lipid layer of the structure, and/or on the surface of the lipid layer. When the lipid membrane structure is represented as microvesicles (e.g., liposomes), the nucleic acid may be encapsulated in the microvesicles.

In this case, the lipid membrane structure with nucleic acid may be in the form of, for example, a dried mixture, an aqueous solvent dispersion, or a dried or frozen product of the dispersion, as with the case of the aforementioned lipid membrane structure.

Next will be described methods for producing various forms of a lipid membrane structure with nucleic acid.

(1) The nucleic-acid-containing composition in the form of dried mixture may be produced by, for example, temporarily dissolving the components of the lipid membrane structure and a nucleic acid in an organic solvent (e.g., chloroform), and then subjecting the resultant mixture to drying under reduced pressure by means of an evaporator, or to spray drying by means of a spray dryer.

(2) The nucleic-acid-containing composition in the form of aqueous solvent dispersion containing the lipid membrane structure and a nucleic acid may be produced through several known methods. In consideration of the mode for retaining the nucleic acid in the lipid membrane structure or the properties of the mixture, the production method may be appropriately selected from among the below-described methods 2-1 to 2-5.

(2-1) Production Method 1

In production method 1, an aqueous solvent is added to the aforementioned dried mixture, and the resultant mixture is emulsified by means of, for example, an emulsifier (e.g., a homogenizer), an ultrasonic emulsifier, or a high-pressure jet emulsifier. For control of size (particle size), extrusion (extrusion typed filtration) may be carried out under high pressure by means of a membrane filter having pores of uniform size. In this production method, firstly, the lipid membrane structure and a nucleic acid must be dissolved in an organic solvent for preparing a dried mixture of the components of the lipid membrane structure and the nucleic acid. This production method is advantageous in that it can utilize to a maximum extent interaction between the components of the lipid membrane structure and the nucleic acid. Even when the lipid membrane structure has a lamellar structure, the nucleic acid can enter between multi-lamellar structures. Thus, this production method is advantageous in that the percent retention of the nucleic acid in the lipid membrane structure can be increased.

(2-2) Production Method 2

In production method 2, the components of the lipid membrane structure are temporarily dissolved in an organic solvent; the organic solvent is removed through evaporation; and an aqueous solvent containing a nucleic acid is added to the resultant dried product, followed by emulsification. For control of size (particle size), extrusion (extrusion typed filtration) may be carried out under high pressure by means of a membrane filter having pores of uniform size. This method is applicable to a nucleic acid which is difficult to dissolve in an organic solvent but can be dissolved in an aqueous solvent. This method is advantageous in that, when the lipid membrane structure is in the form of liposomes, a nucleic acid can also be retained in the internal aqueous phase of the structure.

(2-3) Production Method 3

In production method 3, an aqueous solvent containing a nucleic acid is added to the lipid membrane structure in the form of, for example, liposomes, emulsion, micelles, or lamellar structure which has already been dispersed in an aqueous solvent. This method is applicable to a water-soluble nucleic acid. In this method, a nucleic acid is added to the lipid membrane structure which has already been prepared. Therefore, when a nucleic acid of high molecular weight is employed, the nucleic acid may fail to enter inside the lipid membrane structure and may be present on (bound to) the surface of the lipid membrane structure. As has been known, when production method 3 is applied to the lipid membrane structure in the form of liposomes, a nucleic acid is sandwiched between liposome particles; i.e., a sandwich structure (generally called "complex") is formed. In this production method, since an aqueous dispersion containing only the lipid membrane structure is produced in advance, no attention must be paid to, for example, degradation of a nucleic acid during emulsification, and size (particle size) is readily controlled. Therefore, the nucleic-acid-containing composition can be readily produced through production method 3, as compared with the case of production method 1 or 2.

(2-4) Production Method 4

In production method 4, the lipid membrane structure dispersed in an aqueous solvent is dried, and an aqueous solvent containing a nucleic acid is added to the resultant dried product. Similar to the case of production method 3, production method 4 is applicable to a water-soluble nucleic acid. Production method 4 differs from production method 3 in terms of mode of presence of the lipid membrane structure and a nucleic acid. In production method 4, the lipid membrane structure is temporarily dispersed in an aqueous solvent, and the resultant dispersion is dried. At this stage of the method, the lipid membrane structure is present in the form of a solid lipid membrane fragment. In order to cause such a lipid membrane fragment to be present in a solid form, preferably, as described above, a sugar (or an aqueous solution thereof), more preferably sucrose or lactose (or an aqueous solution thereof), is added to the aqueous solvent employed. When an aqueous solvent containing a nucleic acid is added to the lipid membrane fragment present in a solid form, the lipid membrane fragment is rapidly invaded by water and hydrated, to thereby reconstitute the lipid membrane structure. In this case, the thus-reconstituted lipid membrane structure retains the nucleic acid within its structure.

In production method 3, when a nucleic acid of high molecular weight is employed, the nucleic acid fails to enter inside the lipid membrane structure and is present on (bound to) the surface of the lipid membrane structure. However, production method 4 greatly differs from production method 3 in this regard. That is, in the case of production method 4, the entirety or a portion of a nucleic acid is incorporated in the inside of the lipid membrane structure. In production method 4, since a dispersion containing only the lipid membrane structure is produced in advance, no attention must be paid to degradation of a nucleic acid during emulsification, and size (particle size) is readily controlled. Thus, the nucleic-acid-containing composition can be readily produced through production method 4, as compared with the case of production method 1 or 2. In addition, in production method 4, the lipid membrane structure is temporarily subjected to lyophilization or spray drying. Therefore, this method is advantageous in that, for example, storage stability of the final product (nucleic-acid-containing composition) is readily assured, the size (particle size) of a dried product can be restored by mixing the product with an aqueous solution of a nucleic acid, and a nucleic acid of high molecular weight is readily retained inside the lipid membrane structure.

(2-5) Other Methods

An aqueous solvent dispersion of a mixture of the lipid membrane structure and a nucleic acid may be produced through a method well known as a liposome production method (e.g., the reverse-phase evaporation method). For control of size (particle size), extrusion (extrusion typed filtration) may be carried out under high pressure by means of a membrane filter having pores of uniform size.

(3) When the aforementioned aqueous solvent dispersion of the lipid membrane structure-nucleic acid mixture is further dried, lyophilization, spray drying, or a similar technique may be employed. In this case, the aqueous solvent employed is preferably a solvent containing any of the aforementioned sugars (or an aqueous solution thereof), more preferably sucrose or lactose (or an aqueous solution thereof). When the aqueous solvent dispersion of the lipid membrane structure-nucleic acid mixture is further frozen, a common freezing technique may be employed. In this case, the aqueous solvent employed is preferably a solvent containing a sugar (or an aqueous solution thereof) or a polyhydric alcohol (or an aqueous solution thereof).

The thus-produced composition of the present invention realizes an effective nucleic acid transfection into cells. Therefore, the composition of the present invention can be employed as a nucleic-acid-transfecting agent (e.g., a nucleic-acid-transfecting reagent or drug). When the nucleic-acid-containing composition of the present invention is employed in vitro, for example, the composition may be added to a suspension containing a target cell, or the target cell may be cultured in a medium containing the composition, to thereby transfect the nucleic acid into the target cell. When the nucleic-acid-containing composition of the present invention is employed in vivo, the composition may be administered to a human or a non-human animal. The composition may be orally or parenterally administered. The oral dosage form may be a generally known one; for example, tablet, powder, or granules. The parenteral dosage form may be a generally known one; for example, injection, eye drop, ointment, or suppository. Parenteral administration is preferred, with injection being particularly preferred. Preferably, intravenous injection or local injection into a target cell or organ is carried out.

The nucleic-acid-transfecting composition of the present invention can be employed in a screening method for selecting a substance which increases or inhibits expression of a target nucleic acid, the method including the following steps (1) to (3):

(1) a step of bringing a test substance into contact with a cell into which a target nucleic acid has been transfected;

(2) a step of determining the level of expression of the target nucleic acid in the cell which has been brought into contact with the test substance; and (3) a step of selecting a test substance showing an expression level as determined in (2) above that is higher or lower than the level of expression of the target nucleic acid in a control cell. Specifically, the composition can be employed for transfection of the target nucleic acid into the cell and/or for exposure (introduction) of the cell to the test substance.

Examples of the target nucleic acid include disease-associated genes and plasmid DNA containing such a gene. Examples of the test substance include low-molecular-weight compounds having a molecular weight of less than 10,000, preferably 100 to 2,000, and short nucleotides such as antisense oligonucleotide, antisense DNA, antisense RNA, shRNA, siRNA, and miRNA.

The level of expression of the nucleic acid may be determined through, for example, a known technique such as northern blotting, RT-PCR, or quantitative PCR, or a determination method employing a DNA array.

Examples of the control cell include a cell which is not exposed to the test substance, and a cell into which a short nucleotide or predetermined substance that does not affect the target nucleic acid has been transfected.

EXAMPLES

The present invention will next be described by way of examples, which should not be construed as limiting the invention thereto.

Example 1

Didodecyldimethylammonium bromide (product name: DC-1-12, product of Sogo Pharmaceutical Co., Ltd.), cholesterol (product of Wako Pure Chemical Industries, Ltd.), and dioleoylphosphatidylethanolamine (DOPE, product of NOF corporation) were dissolved in chloroform in proportions (by mole) shown in Table 1, and the resultant solution was dried to solid under reduced pressure, to thereby prepare a lipid mixture. A 9% sucrose solution was added to the lipid mixture, and the mixture was subjected to indirect ultrasonic irradiation by means of a sonicator under heating at 65° C., to thereby yield a crude liposome dispersion having a didodecyldimethylammonium bromide concentration of 2.5 mM. Subsequently, two filters (pore size: 0.22 μm) were placed in an extruder so that the filters were overlapped with each other, and the crude liposome dispersion was subjected to extrusion (extrusion typed filtration) under heating at about 65° C. and pressurized conditions, so as to prepare liposomes having a uniform particle size. Thereafter, in a manner similar to that described above, the resultant dispersion was extruded through a filter (pore size: 0.1 μm), to thereby yield a dispersion of empty liposomes. The liposome dispersion was dispensed into 2-mL vials (1 mL each), followed by lyophilization, to thereby yield lyophilized liposomes (Formulation Examples 1 and 2).

The mean particle size and zeta potential of the liposomes of Formulation Examples 1 and 2 were determined by means of NICOMP 380ZLS (product of Particle Sizing Systems). As a result, the liposomes of Formulation Examples 1 and 2 were found to have mean particle sizes of 141 nm and 94 nm, and zeta potentials of 22 mV and 26 mV, respectively.

TABLE 1

| Formulation Example | Proportions by mole (%) | | |
|---|---|---|---|
| | DOPE | Cholesterol | DC-1-12 |
| Formulation Example 1 | 28.6 | 0 | 71.4 |
| Formulation Example 2 | 30 | 30 | 40 |

Example 2

The procedure of Example 1 was repeated, except that didodecyldimethylammonium bromide was replaced with dimethylditetradecylammonium bromide (product name: DC-1-14, product of Sogo Pharmaceutical Co., Ltd.), to thereby yield lyophilized liposomes (Formulation Examples 3 and 4) shown in Table 2.

The mean particle size and zeta potential of the liposomes of Formulation Examples 3 and 4 were determined in a manner similar to that described in Example 1. As a result, the liposomes of Formulation Examples 3 and 4 were found to have mean particle sizes of 122 nm and 83 nm, and zeta potentials of 24 mV and 13 mV, respectively.

TABLE 2

| Formulation Example | Proportions by mole (%) | | |
|---|---|---|---|
| | DOPE | Cholesterol | DC-1-14 |
| Formulation Example 3 | 28.6 | 0 | 71.4 |
| Formulation Example 4 | 30 | 30 | 40 |

Example 3

The procedure of Example 1 was repeated, except that didodecyldimethylammonium bromide was replaced with dihexadecyldimethylammonium bromide (product name: DC-1-16, product of Sogo Pharmaceutical Co., Ltd.), to thereby yield lyophilized liposomes (Formulation Examples 5 and 6) shown in Table 3.

The mean particle size and zeta potential of the liposomes of Formulation Examples 5 and 6 were determined in a manner similar to that described in Example 1. As a result, the liposomes of Formulation Examples 5 and 6 were found to have mean particle sizes of 122 nm and 159 nm, and zeta potentials of 26 mV and 20 mV, respectively.

TABLE 3

| Formulation Example | Proportions by mole (%) | | |
|---|---|---|---|
| | DOPE | Cholesterol | DC-1-16 |
| Formulation Example 5 | 28.6 | 0 | 71.4 |
| Formulation Example 6 | 30 | 30 | 40 |

Control Examples

The procedure of Example 1 was repeated, except that didodecyldimethylammonium bromide was replaced with dioctadecyldimethylammonium bromide (product name: DC-1-18, product of Sogo Pharmaceutical Co., Ltd.), to thereby yield lyophilized liposomes (Control Examples 1 and 2) shown in Table 4.

The mean particle size and zeta potential of the liposomes of Control Examples 1 and 2 were determined in a manner similar to that described in Example 1. As a result, the liposomes of Control Examples 1 and 2 were found to have mean particle sizes of 94 nm and 177 nm, and zeta potentials of 26 mV and 22 mV, respectively.

TABLE 4

| Formulation Example | Proportions by mole (%) | | |
|---|---|---|---|
| | DOPE | Cholesterol | DC-1-18 |
| Control Example 1 | 28.6 | 0 | 71.4 |
| Control Example 2 | 30 | 30 | 40 |

Test Example 1

Test for Transfection of Nucleic Acid into CHO Cells

An aqueous solution of siRNA having the below-described sequences (1 pmol/μL) was 6.25-fold diluted with an F-12 HAM medium, to thereby prepare a siRNA-diluted solution. Separately, the lyophilized liposome product of Formulation Example 1 was reconstituted with an appropriate amount of water to give a solution having a DC-1-12 concentration of about 1 mM.

```
                                             (SEQ ID NO: 1)
Sense:      5'-ACAUCACGUACGCGGAAUACUUCGA-AG-3'

(SEQ ID NO: 2)
Antisense:  3'-UA-UGUAGUGCAUGCGCCUUAUGAAGCU-5'
```

The thus-obtained solution was 3.47-, 20.8- or 125-fold diluted with an F12 Ham medium. Each of the thus-diluted solutions was added to and mixed with an equiamount of the siRNA-diluted solution, to thereby form a siRNA/liposome complex. In this case, the ratio of the amount of DC-1-12-derived cations to the amount of siRNA-derived anions is about 33 (for the case of 3.47-fold dilution), about 6 (for the case of 20.8-fold dilution), or about 1 (for the case of 125-fold dilution). Subsequently, the resultant solution was added to and mixed with an equiamount of a 20%-FBS-containing F-12 HAM medium, to thereby prepare a siRNA/liposome-complex-containing medium. Medium for CHO (pMAM-luc) cells (JCRB0136.1, obtained from Human Science Research Resources Bank) was replaced with the siRNA/liposome-complex-containing medium, to thereby initiate transfection. After culturing at 37° C. and 5% $CO_2$ for about 41 hours, the medium was replaced with an F-12 HAM medium containing 1 μM dexamethasone and 10% FBS. After culturing at 37° C. and 5% $CO_2$ for about six to about eight hours, cells were observed under a microscope, and cytotoxicity was evaluated according to the following scores (−: cells cover about 85 to about 100% of the field of view, and no trace of damage due to toxicity is observed; ±: cells cover about 85 to about 100% of the field of view, but some trace of damage due to toxicity is observed; +: cells cover about 70 to about 80% of the field of view; ++: cells cover about 50 to about 70% of the field of view; and +++: cells cover only less than about 50% of the field of view). The results are shown in Table 5. After removal of the medium, the cells were washed with PBS. Subsequently, the cells were lysed with PLB, and then luciferase activity was determined. For a control, the above-described experiment was repeated, except that water was employed in place of the siRNA solution. The experiment was carried out for the lyophilized liposome products of Formulation Examples 2 to 6 and Control Examples 1 and 2 in the same manner as in the case of Formulation Example 1. Percent knockdown (%) was calculated on the basis of the following formula (1). The results are shown in Table 5.

$$100 \times (\text{luciferase activity in the presence of siRNA}) / (\text{luciferase activity in the absence of siRNA}) \quad \text{Formula (1):}$$

Separately, for a positive control, percent knockdown was evaluated by use of Lipofectamine 2000 (trade name: product of Invitrogen).

The siRNA solution (1 pmol/μL) was 2.5-fold diluted with an F12 Ham medium, to thereby prepare a siRNA-diluted solution. Separately, Lipofectamine 2000 (trade name: product of Invitrogen) was 50-fold diluted with an F-12 HAM medium. The thus-diluted solution was added to an equiamount of the siRNA-diluted solution, to thereby prepare a siRNA/Lipofectamine 2000-containing medium. The thus-prepared medium (20 μL) was added to separately cultured CHO (pMAM-luc) cells (medium amount: 100 μL), to thereby initiate transfection. After culturing at 37° C. and 5% $CO_2$ for about 41 hours, the medium was replaced with an F12-Ham medium containing 1 μM dexamethasone and 10% FBS. After culturing at 37° C. and 5% $CO_2$ for about seven hours, cells were observed under a microscope, and cytotoxicity was evaluated according to the aforementioned scores. After removal of the medium, the cells were washed with PBS(−). Subsequently, the cells were lysed with 1×PLB, and then luciferase activity was determined. For a control, the above-described experiment was repeated, except that water was employed in place of the siRNA solution, and percent knockdown (%) was calculated on the basis of formula (1). As a result, cytotoxicity was found to be low (score: −), but white spots were observed in the cells. Percent knockdown was found to be 41%.

Test Example 2

Test for Transfection of Nucleic Acid into HeLa Cells

An aqueous solution of siRNA having the below-described sequences (1 pmol/μL) was 6.25-fold diluted with a Dulbecco's modified Eagle's medium (hereinafter abbreviated as a "DMEM medium"), to thereby prepare a siRNA-diluted solution. Separately, the lyophilized liposome product of Formulation Example 1 was reconstituted with an appropriate amount of water to give a solution having a DC-1-12 concentration of about 1 mM.

Sense:     5'-ACAUCACUUACGCUGAGUACUUCGA-AG-3' (SEQ ID NO: 3)

Antisense: 3'-UA-UGUAGUGAAUGCGACUCAUGAAGCU-5' (SEQ ID NO: 4)

The thus-obtained solution was 28.8-, 115-, or 215-fold diluted with a DMEM medium. Each of the thus-diluted solutions was added to and mixed with an equiamount of the siRNA-diluted solution, to thereby form a siRNA/liposome complex. In this case, the ratio of the amount of DC-1-12-derived cations to the amount of siRNA-derived anions is about 4 (for the case of 28.8-fold dilution), about 1 (for the case of 115-fold dilution), or about 0.5 (for the case of 215-fold dilution). Subsequently, the resultant solution was added to and mixed with an equiamount of a 20%-FBS-containing DMEM medium, to thereby prepare a siRNA/liposome-complex-containing medium. Medium for cells of the NFAT Reporter HeLa Stable Cell Line (product of Panomics) was replaced with the siRNA/liposome-complex-containing medium, to thereby initiate transfection. After culturing at 37° C. and 5% $CO_2$ for about 18 hours, the medium was replaced with a DMEM medium containing 10 ng/mL PMA, 0.5 µM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. The results are shown in Table 5. After removal of the medium, the cells were washed with PBS. Subsequently, the cells were lysed with PLB, and then luciferase activity was determined. For a control, the above-described experiment was repeated, except that water was employed in place of the siRNA solution. The experiment was carried out for the lyophilized liposome products of Formulation Examples 2 to 6 and Control Examples 1 and 2 in the same manner as in the case of Formulation Example 1. Percent knockdown (%) was calculated on the basis of formula (1). The results are shown in Table 5.

Separately, for a positive control, percent knockdown was evaluated by use of Lipofectamine 2000 (trade name: product of Invitrogen).

The siRNA solution (1 pmol/µL) was 2.5-fold diluted with a DMEM medium, to thereby prepare a siRNA-diluted solution. Separately, Lipofectamine 2000 was 100-fold diluted with a DMEM medium. The thus-diluted solution was added to an equiamount of the siRNA-diluted solution, to thereby prepare a siRNA/Lipofectamine 2000-containing medium. The thus-prepared medium (20 µL) was added to a medium (100 µL) of separately cultured NFAT Reporter HeLa Stable Cell Line (product of Panomics), to thereby initiate transfection. After culturing at 37° C. and 5% $CO_2$ for about 18 hours, the medium was replaced with a DMEM medium containing 10 ng/mL PMA, 0.5 µM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. After removal of the medium, the cells were washed with PBS(−). Subsequently, the cells were lysed with 1×PLB, and then luciferase activity was determined. For a control, the above-described experiment was repeated, except that water was employed in place of the siRNA solution, and percent knockdown (%) was calculated on the basis of formula (1). As a result, cytotoxicity was found to be low (score: −), but white spots were observed in the cells. Percent knockdown was found to be 9%.

TABLE 5

| | Cells | | | | | |
|---|---|---|---|---|---|---|
| | CHO | | | HeLa | | |
| Cation/Anion | 1 | 6 | 33 | 0.5 | 1 | 4 |
| Formulation Example 1 | 99 | 97 | 97 | 101 | 94 | 97 |
| | − | +++ | +++ | − | − | +++ |
| Formulation Example 2 | 102 | 99 | 101 | 78 | 88 | 102 |
| | − | +++ | +++ | − | − | +++ |
| Formulation Example 3 | 99 | 73 | 110 | 32 | 32 | 19 |
| | − | − | +++ | − | − | − |
| Formulation Example 4 | 77 | 32 | 108 | 9 | 10 | 6 |
| | − | − | +++ | − | − | ± |
| Formulation Example 5 | 87 | 89 | 109 | 35 | 35 | 11 |
| | − | − | +++ | − | − | ± |
| Formulation Example 6 | 71 | 76 | 63 | 10 | 12 | 18 |
| | − | − | +++ | − | − | + |
| Control Example 1 | 93 | 79 | 27 | 70 | 63 | 22 |
| | − | − | ++ | − | − | − |
| Control Example 2 | 100 | 103 | 31 | 45 | 30 | 19 |
| | − | − | +++ | − | − | ± |

Upper: percent knockdown (%), Lower: cytotoxicity score

As shown in Table 5, the compositions of Formulation Examples 1 to 6 (i.e., the compositions of the present invention) exhibited excellent nucleic-acid-transfecting performance (percent knockdown) and low cytotoxicity. Particularly, the composition of Formulation Example 4 exhibited excellent nucleic-acid-transfecting performance and low cytotoxicity even in the case of CHO cells, into which a nucleic acid is difficult to transfect even with Lipofectamine 2000.

Example 4

In a manner similar to that described in Example 2, lyophilized liposomes shown in Table 6 were prepared (Production Examples A to O).

In a manner similar to that described in Example 1, the mean particle size and zeta potential of the liposomes of Production Examples A to O were determined. The mean particle sizes were found to be as follows: 98 nm (Production Example A), 133 nm (Production Example B), 150 nm (Production Example C), 319 nm (Production Example D), 112 nm (Production Example E), 107 nm (Production Example F), 116 nm (Production Example G), 58 nm (Production Example H), 71 nm (Production Example I), 89 nm (Production Example J), 111 nm (Production Example K), 84 nm (Production Example L), 63 nm (Production Example M), 55 nm (Production Example N), and 50 nm (Production Example O). The zeta potentials were found to be as follows: 18 mV (Production Example A), 27 mV (Production Example B), 23 mV (Production Example C), 26 mV (Production Example D), 27 mV (Production Example E), 25 mV (Production Example F), 16 mV (Production Example G), 17 mV (Production Example H), 22 mV (Production Example I), 19 mV (Production Example J), 23 mV (Production Example K), 24 mV (Production Example L), 22 mV (Production Example M), 18 mV (Production Example N), and 24 mV (Production Example O).

TABLE 6

| | Proportions by mole (%) | | |
|---|---|---|---|
| Formulation Example | DOPE | Cholesterol | DC-1-14 |
| Production Example A | 0 | 50 | 50 |
| Production Example B | 10 | 50 | 40 |
| Production Example C | 20 | 50 | 30 |

TABLE 6-continued

| Formulation Example | Proportions by mole (%) | | |
|---|---|---|---|
| | DOPE | Cholesterol | DC-1-14 |
| Production Example D | 30 | 50 | 20 |
| Production Example E | 0 | 32 | 68 |
| Production Example F | 15 | 32 | 53 |
| Production Example G | 45 | 32 | 23 |
| Production Example H | 5 | 16 | 79 |
| Production Example I | 24 | 16 | 60 |
| Production Example J | 42 | 16 | 42 |
| Production Example K | 63 | 16 | 21 |
| Production Example L | 20 | 0 | 80 |
| Production Example M | 40 | 0 | 60 |
| Production Example N | 60 | 0 | 40 |
| Production Example O | 80 | 0 | 20 |

Test Example 3

Test for Transfection of Nucleic Acid into CHO Cells

The siRNA solution (1 pmol/μL) employed in Test Example 1 was 6.25-fold diluted with an F-12 HAM medium, to thereby prepare a siRNA-diluted solution. Separately, the lyophilized liposome product of Production Example A was reconstituted with an appropriate amount of water to give a solution having a DC-1-14 concentration of about 1 mM. The thus-obtained solution was 14.4-, 19.2-, or 28.8-fold diluted with an F-12 HAM medium. Each of the thus-diluted solutions was added to and mixed with an equiamount of the siRNA-diluted solution, to thereby form a siRNA/liposome complex. In this case, the ratio of the amount of DC-1-14-derived cations to the amount of siRNA-derived anions is about 8 (for the case of 14.4-fold dilution), about 6 (for the case of 19.2-fold dilution), or about 4 (for the case of 28.8-fold dilution). Subsequently, the resultant solution was added to and mixed with an equiamount of a 20%-FBS-containing F-12 HAM medium, to thereby prepare a siRNA/liposome-complex-containing medium. Medium for CHO (pMAM-luc) cells (JCRB0136.1, obtained from Human Science Research Resources Bank) was replaced with the siRNA/liposome-complex-containing medium, to thereby initiate transfection. After culturing at 37° C. and 5% $CO_2$ for about 41 hours, the medium was replaced with an F-12 HAM medium containing 1 μM dexamethasone and 10% FBS. After culturing at 37° C. and 5% $CO_2$ for about six to about eight hours, cells were observed under a microscope, and cytotoxicity was evaluated according to the aforementioned scores in a manner similar to that described in Test Example 1. After removal of the medium, the cells were washed with PBS(−). Subsequently, the cells were lysed with 1×PLB, and then luciferase activity was determined. For a control, the above-described experiment was repeated, except that water was employed in place of the siRNA solution. The experiment was carried out for the lyophilized liposome products of Production Examples B to O and Formulation Examples 3 and 4 in the same manner as in the case of Production Example A. Percent knockdown (%) was calculated on the basis of formula (1). The results are shown in Table 7.

Separately, for a positive control, Lipofectamine 2000 (trade name: product of Invitrogen) was employed, and, in a manner similar to that described in Test Example 1, cytotoxicity was evaluated according to the aforementioned scores, and percent knockdown (%) was calculated.

As a result, cytotoxicity was found to be low (score: −), but white spots were observed in the cells. Percent knockdown was found to be 32.1±9.4%.

TABLE 7

| Formulation Example | DC-1-14/ DOPE | DC-1-14 concentration (pmol/well) | | |
|---|---|---|---|---|
| | | 864 | 1296 | 1728 |
| Production Example A | — | 71.5 − | 45.8 − | 120.9 + |
| Production Example B | 4.00 | 69.1 − | 31.2 − | 41.4 + |
| Production Example C | 1.50 | 53.4 − | 38.0 − | 36.6 ++ |
| Production Example D | 0.67 | 79.5 − | 66.3 ± | 83.7 − |
| Production Example E | — | 102.3 − | 71.0 − | 106.8 +++ |
| Production Example F | 3.53 | 38.4 − | 25.1 − | 81.6 +++ |
| Formulation Example 4 | 1.33 | 27.3 − | 26.3 ± | 49.6 ++ |
| Production Example G | 0.51 | 37.4 − | 25.6 − | 80.4 − |
| Production Example H | 15.80 | 96.4 − | 120.3 ± | 77.9 +++ |
| Production Example I | 2.50 | 64.1 − | 40.3 − | 56.0 ++ |
| Production Example J | 1.00 | 23.7 − | 12.2 − | 27.2 ++ |
| Production Example K | 0.33 | 48.5 − | 24.1 − | 88.4 − |
| Production Example L | 4.00 | 83.2 − | 102.2 ± | 65.0 +++ |
| Formulation Example 3 | 2.50 | 85.9 − | 44.9 − | 88.5 +++ |
| Production Example M | 1.50 | 64.7 − | 23.3 ± | 87.8 ++ |
| Production Example N | 0.67 | 19.2 − | 14.8 +++ | 23.9 + |
| Production Example O | 0.25 | 51.6 − | 28.2 − | 115.5 − |

Upper: percent knockdown (%), Lower: cytotoxicity score

Test Example 4

Test for Transfection of Nucleic Acid into HeLa Cells

The siRNA solution (1 pmol/μL) employed in Test Example 2 was 6.25-fold diluted with a DMEM medium, to thereby prepare a siRNA-diluted solution. Separately, the lyophilized liposome product of Production Example A was reconstituted with an appropriate amount of water to give a solution having a DC-1-14 concentration of about 1 mM. The thus-obtained solution was 28.8-, 57.7-, 115-, or 500-fold diluted with a DMEM medium. Each of the thus-diluted solutions was added to and mixed with an equiamount of the siRNA-diluted solution, to thereby form a siRNA/liposome complex. Subsequently, the resultant solution was added to and mixed with an equiamount of a 20%-FBS-containing DMEM medium, to thereby prepare a siRNA/liposome-complex-containing medium. Medium for cells of the NFAT Reporter HeLa Stable Cell Line (product of Panomics) was replaced with the siRNA/liposome-complex-containing medium, to thereby initiate transfection. After culturing at 37° C. and 5% $CO_2$ for about 18 hours, the medium was replaced with a DMEM medium containing 10 ng/mL PMA, 0.5 μM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. After removal of the medium, the cells were washed with PBS. Subsequently, the cells were lysed with PLB, and then luciferase activity was determined. For a control, the above-described experiment was repeated, except that water was employed in place of the siRNA solution. The experiment was carried out for the lyophilized liposome products of Production Examples B to O and Formulation Examples 3 and 4 in the same manner as in the case of Production Example A. Percent knockdown (%) was calculated on the basis of formula (I). The results are shown in Table 8.

Separately, for a positive control, Lipofectamine 2000 (trade name: product of Invitrogen) was employed, and, in a manner similar to that described in Test Example 2, cytotoxicity was evaluated according to the aforementioned scores, and percent knockdown (%) was calculated.

As a result, cytotoxicity was found to be low (score: −), but white spots were observed in the cells. Percent knockdown was found to be 8.9±2.1%.

TABLE 8

| Formulation Example | DC-1-14/ DOPE | DC-1-14 concentration (pmol/well) | | | |
|---|---|---|---|---|---|
| | | 50 | 216 | 432 | 864 |
| Production Example A | — | 89.7 − | 30.6 − | 23.7 − | 20.8 ± |
| Production Example B | 4.00 | 10.2 − | 8.1 − | 5.3 − | 20.2 +++ |
| Production Example C | 1.50 | 37.3 − | 6.3 − | 7.6 − | 15.6 ++ |
| Production Example D | 0.67 | 85.9 − | 66.4 ± | 15.4 − | 72.8 − |
| Production Example E | — | 117.3 − | 69.6 − | 50.1 − | 37.6 + |
| Production Example F | 3.53 | 28.1 − | 6.1 − | 5.5 − | 36.5 +++ |
| Formulation Example 4 | 1.33 | 18.6 − | 8.5 − | 5.2 − | 14.1 ++ |
| Production Example G | 0.51 | 118.3 − | 21.6 − | 8.3 − | 44.4 − |
| Production Example H | 15.80 | 64.7 − | 27.1 − | 40.4 − | 34.7 + |
| Production Example I | 2.50 | 23.4 − | 13.7 − | 10.2 − | 25.6 ± |
| Production Example J | 1.00 | 36.8 − | 8.2 − | 6.5 − | 8.2 + |
| Production Example K | 0.33 | 83.1 − | 24.5 − | 10.4 − | 86.9 − |
| Production Example L | 4.00 | 50.5 − | 25.0 − | 14.8 − | 36.8 + |
| Formulation Example 3 | 2.50 | 42.9 − | 28.0 − | 25.8 + | 95.5 + |
| Production Example M | 1.50 | 65.3 − | 44.7 − | 28.4 + | 47.7 ± |
| Production Example N | 0.67 | 33.9 − | 8.6 − | 6.3 − | 8.4 + |
| Production Example O | 0.25 | 89.6 − | 56.7 − | 43.5 − | 72.2 − |

Upper: percent knockdown (%), Lower: cytotoxicity score

As shown in Tables 7 and 8, the compositions of Production Examples B to D and F to O and Formulation Example 4 (i.e., the compositions of the present invention) exhibited excellent nucleic-acid-transfecting performance and low cytotoxicity.

These data indicate that when the concentration of the di($C_{12-16}$ alkyl)dimethylammonium halide employed in the present invention is appropriately determined, the resultant nucleic-acid-transfecting composition exhibits more excellent performance in terms of transfection of nucleic acid and cytotoxicity.

As shown in Tables 7 and 8, the compositions of Production Examples C, J, and N and Formulation Example 4 (in particular, the compositions of Production Examples C and J and Formulation Example 4) exhibited excellent nucleic-acid-transfecting performance.

Test Example 5

Test for Transfection of Nucleic Acid into HeLa Cells

HeLa cells were inoculated into a 96-well plate (7,500 cells/100 µL/well), followed by culturing for about 24 hours. DNA (pCMV-SPORT-βgal) was diluted with a DMEM medium, to thereby prepare a DNA-diluted solution having a DNA concentration of 8 µg/mL (for the case of 200 ng/well). Separately, the lyophilized liposome product of Formulation Example 2, 4, 6, or Control Example 2 was reconstituted with an appropriate amount of water for injection to give a solution having a cationic lipid concentration of about 1 mM. The thus-obtained solution or Lipofectamine 2000 as a positive control (product of Invitrogen) was diluted with a DMEM medium so that the amount of the reconstituted liposome solution or Lipofectamine 2000 added to cells was "Amount of liposomes added (µL/well)" shown in Table 9 or 10. Immediately after dilution, the DNA-diluted solution (25 µL) was added to and mixed with the liposome-diluted solution (25 µL), and the mixture was allowed to stand still at room temperature for 30 minutes, to thereby form a DNA/liposome complex. The DNA/liposome complex (50 µL) was added to the inoculated HeLa cells (about 70 to about 90% confluent), to thereby initiate transfection. After culturing at 37° C. and 5% $CO_2$ for one hour, a 10% FBS/DMEM medium (100 µL) was added to the culture liquid, followed by culturing at 37° C. and 5% $CO_2$ for about 21 hours. Thereafter, cells were observed under a microscope, and cytotoxicity was evaluated according to the following scores (−: the density and morphology of cells are similar to those of cells contained in a liposome-free well (i.e., a well containing only cells and DNA); +: about 10 to about 20% of cells are rounded; ++: about 30 to about 40% of cells are rounded; +++: about 50 to about 60% of cells show morphological abnormality, or cell density is slightly reduced; and ++++: most cells show morphological abnormality, and cell density is considerably reduced).

The culture supernatant was removed, and the cells were washed with PBS(−). Thereafter, determination of β-galactosidase (hereinafter may be abbreviated as "β-gal") activity, quantitative determination of protein, and viable cell counting were carried out as described below. The results are shown in Tables 9 and 10.

(1) Determination of β-gal activity and quantitative determination of protein

After complete removal of PBS through suction, a lysis buffer (30 µL) was added to the cells, and the mixture was stirred and then allowed to stand still at −80° C. for 30 minutes or longer for freezing. After rapid thawing in a water bath at 37° C., the mixture was again allowed to stand still at −80° C. for 30 minutes or longer for freezing, followed by rapid thawing in a water bath at 37° C. Thereafter, centrifugation was carried out (2,000 g×10 minutes), and the resultant supernatant (sample) (10 µL) was added to a 96-well microplate.

Determination of β-gal activity was carried out by means of a β-gal assay kit (product of Invitrogen). Specifically, standard β-galactosidase was diluted with a lysis buffer to give a solution having a β-gal concentration of 4, 2, 1, 0.5, or 0.25 U/mL. A 2-Me-containing cleavage buffer was added (50 µL/well) to the sample or each of the standard-diluted solutions (10 µL), and 4 mg/mL aqueous ONPG solution was added (17 µL/well), followed by incubation at 37° C. for 30 minutes. After completion of incubation, a stop buffer was added (120 µL/well) for termination of reaction, and absorbance was measured at 405 nm.

Quantitative determination of protein was carried out by means of a BCA protein assay kit (product of PIERS). Specifically, standard BSA was diluted with a lysis buffer to give a solution having a BSA concentration of 500, 300, 100, 50, or 25 µg/mL. A WR solution was added (200 µL/well) to the sample or each of the standard-diluted solutions (10 µl), followed by stirring for 30 seconds and incubating at 37° C. for one hour. After cooling to room temperature, absorbance was measured at 562 nm.

(2) Viable Cell Counting

Viable cell counting was carried out by means of a Cell Counting Kit (product of Dojindo Laboratories) based on WST-1 assay. Specifically, a 10% FBS/DMEM medium (100 µL) was added to the cells washed with PBS(−), and then a WST-1 solution (10 µL) was added thereto, followed by stirring and culturing at 37° C. and 5% $CO_2$ for four hours. Thereafter, absorbance was measured at 450 nm. A cell count vs. A450 standard curve was prepared on the basis of a separately prepared dilution series of different numbers of inoculated cells, and the number of viable cells was estimated by use of the standard curve. Cell survival rate was calculated for each well on the basis of the number of viable cells in a liposome-free well (i.e., a well containing only cells and DNA) (taken as 100%).

Test Example 6

Test for Transfection of Nucleic Acid into HT1080 Cells

The procedure of Test Example 5 was repeated, except that HeLa cells were replaced with HT1080 cells. In a manner similar to that described in Test Example 5, cytotoxicity was evaluated according to the aforementioned scores, and determination of β-gal activity, quantitative determination of protein, and viable cell counting were carried out. The results are shown in Tables 9 and 10.

TABLE 9

| Cells | Formulation Example | β-gal (mU/well) Amount of liposomes added (µL/well) | | | | | | Cell survival rate relative to that in liposome-free well Amount of liposomes added (µL/well) | | | | | |
|---|---|---|---|---|---|---|---|---|---|---|---|---|---|
| | | 0.19 | 0.38 | 0.8 | 1.5 | 3.0 | 6.0 | 0.19 | 0.38 | 0.8 | 1.5 | 3.0 | 6.0 |
| HeLa | LFA2000 | 39.0 | 71.2 | 85.7 | 49.4 | 4.0 | — | 63% | 55% | 33% | 9% | 1% | — |
| | Formulation Example 2 | 0.0 | 0.2 | 0.6 | 0.8 | 2.1 | 0.1 | 85% | 76% | 72% | 76% | 32% | 0% |
| | Formulation Example 4 | 18.9 | 18.1 | 15.2 | 5.6 | 2.4 | 0.1 | 74% | 63% | 36% | 16% | 13% | 9% |
| | Formulation Example 6 | 4.3 | 7.3 | 10.2 | 2.4 | 0.2 | 0.0 | 71% | 58% | 36% | 8% | 1% | 0% |
| | Control Example 2 | 0.0 | 0.4 | 0.9 | 2.7 | 3.0 | 0.4 | 95% | 88% | 53% | 65% | 21% | 2% |
| HT1080 | LFA2000 | 42.8 | 63.3 | 64.2 | 24.3 | 2.6 | — | 55% | 61% | 17% | 6% | 2% | — |
| | Formulation Example 2 | 0.0 | 0.2 | 0.5 | 0.3 | 0.0 | 0.0 | 84% | 84% | 90% | 99% | 6% | 1% |
| | Formulation Example 4 | 34.3 | 59.8 | 70.0 | 46.5 | 8.9 | 0.0 | 63% | 57% | 49% | 23% | 10% | 5% |
| | Formulation Example 6 | 2.2 | 6.6 | 9.9 | 13.6 | 6.0 | 0.0 | 97% | 78% | 88% | 55% | 11% | 4% |
| | Control Example 2 | 0.0 | 0.0 | 0.1 | 0.5 | 4.9 | 0.0 | 108% | 109% | 107% | 88% | 28% | 5% |

LFA2000: Lipofectamine 2000

TABLE 10

| Cells | Formulation Example | Cytotoxicity score Amount of liposomes added (µL/well) | | | | | | Total protein amount (µg/well) Amount of liposomes added (µL/well) | | | | | |
|---|---|---|---|---|---|---|---|---|---|---|---|---|---|
| | | 0.19 | 0.38 | 0.8 | 1.5 | 3.0 | 6.0 | 0.19 | 0.38 | 0.8 | 1.5 | 3.0 | 6.0 |
| HeLa | LFA2000 | 1.0 | 2.0 | 2.8 | 4.0 | 5.0 | — | 9.5 | 7.9 | 6.1 | 2.6 | 0.7 | — |
| | Formulation Example 2 | 0.0 | 0.0 | 0.5 | 0.8 | 3.0 | 5.0 | 10.3 | 10.7 | 9.1 | 8.4 | 3.9 | 0.8 |
| | Formulation Example 4 | 0.8 | 1.0 | 3.0 | 4.0 | 4.0 | 5.0 | 8.9 | 8.6 | 5.6 | 2.4 | 1.9 | 2.0 |
| | Formulation Example 6 | 1.0 | 2.0 | 3.0 | 4.0 | 4.0 | 5.0 | 10.0 | 6.9 | 4.5 | 2.5 | 0.8 | 0.5 |
| | Control Example 2 | 0.0 | 0.5 | 0.8 | 1.5 | 3.0 | 5.0 | 11.7 | 10.4 | 11.2 | 7.9 | 4.1 | 2.6 |
| HT1080 | LFA2000 | 0.8 | 1.5 | 3.0 | 4.5 | 5.0 | — | 8.4 | 6.6 | 4.4 | 1.5 | 0.8 | — |
| | Formulation Example 2 | 0.0 | 0.0 | 0.0 | 0.5 | 3.0 | 4.0 | 9.6 | 11.0 | 10.3 | 9.0 | 1.8 | 1.0 |
| | Formulation Example 4 | 0.5 | 1.0 | 2.0 | 3.0 | 4.0 | 5.0 | 8.6 | 8.6 | 7.8 | 4.1 | 2.8 | 2.0 |
| | Formulation Example 6 | 0.0 | 0.0 | 0.5 | 1.5 | 3.0 | 4.0 | 9.6 | 11.6 | 10.4 | 8.4 | 3.8 | 1.7 |

TABLE 10-continued

|  | Formulation | Cytotoxicity score Amount of liposomes added (μL/well) | | | | | | Total protein amount (μg/well) Amount of liposomes added (μL/well) | | | | | |
|---|---|---|---|---|---|---|---|---|---|---|---|---|---|
|  |  | 0.19 | 0.38 | 0.8 | 1.5 | 3.0 | 6.0 | 0.19 | 0.38 | 0.8 | 1.5 | 3.0 | 6.0 |
| Cells | Example | | | | | | | | | | | | |
|  | Control Example 2 | 0.0 | 0.5 | 0.5 | 1.0 | 2.0 | 4.0 | 11.0 | 11.5 | 11.2 | 9.6 | 6.8 | 2.4 |

LFA2000: Lipofectamine 2000

As shown in Tables 9 and 10, among the compositions of the present invention, particularly, the composition of Formulation Example 2 exhibited excellent nucleic-acid-transfecting performance and low cytotoxicity.

Test Example 7

Test for Transfection of Nucleic Acid into HeLa Cells

The procedure of Test Example 5 was repeated for the lyophilized liposome products of Formulation Examples 3 and 4 and Production Examples A to O. In a manner similar to that described in Test Example 5, cytotoxicity was evaluated according to the aforementioned scores, and determination of β-gal activity, quantitative determination of protein, and viable cell counting were carried out. The results are shown in Tables 11 and 12.

Test Example 8

Test for Transfection of Nucleic Acid into HT1080 Cells

The procedure of Test Example 6 was repeated for the lyophilized liposome products of Formulation Examples 3 and 4 and Production Examples A to O. In a manner similar to that described in Test Example 6, cytotoxicity was evaluated according to the aforementioned scores, and determination of β-gal activity, quantitative determination of protein, and viable cell counting were carried out. The results are shown in Tables 11 and 12.

TABLE 11

|  | Formulation | β-gal activity (mU/well) Amount of liposomes added (μL/well) | | | | | | Cell survival rate relative to that in liposome-free well Amount of liposomes added (μL/well) | | | | | |
|---|---|---|---|---|---|---|---|---|---|---|---|---|---|
| Cells | Example | 0.09 | 0.19 | 0.4 | 0.8 | 1.5 | 3.0 | 0.09 | 0.19 | 0.4 | 0.8 | 1.5 | 3.0 |
| HeLa | LFA2000 | — | 85.3 | 98.4 | 99.1 | 69.0 | 9.8 | — | 53% | 37% | 17% | 5% | 3% |
|  | Production Example A | 0.1 | 0.3 | 0.5 | 0.8 | 5.0 | 1.3 | 98% | 88% | 101% | 92% | 32% | 54% |
|  | Production Example B | 0.3 | 2.4 | 3.8 | 3.4 | 10.6 | 8.8 | 96% | 88% | 119% | 97% | 6% | 5% |
|  | Production Example C | 5.1 | 16.7 | 33.9 | 38.7 | 16.5 | 4.6 | 92% | 73% | 92% | 41% | 11% | 6% |
|  | Production Example D | 0.0 | 0.1 | 0.3 | 0.4 | 2.1 | 7.7 | 95% | 91% | 126% | 91% | 88% | 28% |
|  | Production Example E | −0.1 | 0.0 | 0.0 | −0.1 | 0.1 | 0.1 | 93% | 89% | 98% | 78% | 73% | 55% |
|  | Production Example F | 0.5 | 0.9 | 3.2 | 5.4 | 14.0 | 4.9 | 98% | 87% | 106% | 67% | 10% | 10% |
|  | Production Example G | 0.0 | 0.1 | 0.7 | 2.4 | 4.6 | 6.2 | 87% | 82% | 129% | 85% | 73% | 13% |
|  | Production Example H | 0.1 | 0.1 | 0.2 | 0.3 | 0.2 | 0.1 | 95% | 110% | 103% | 60% | 76% | 21% |
|  | Production Example I | 1.4 | 0.3 | 0.5 | 3.9 | 6.0 | 2.2 | 122% | 123% | 119% | 76% | 32% | 22% |
|  | Production Example J | 5.3 | 17.1 | 50.4 | 39.4 | 10.7 | 4.3 | 104% | 97% | 119% | 67% | 15% | 6% |
|  | Production Example K | 0.0 | 0.1 | 1.1 | 1.2 | 3.8 | 8.3 | 108% | 99% | 175% | 150% | 78% | 19% |
|  | Production Example L | 0.0 | 0.0 | 0.1 | 0.4 | 0.1 | 0.1 | 125% | 116% | 184% | 166% | 83% | 26% |
|  | Production Example M | 1.6 | 3.7 | 10.9 | 31.5 | 13.1 | 4.7 | 105% | 100% | 159% | 69% | 14% | 27% |
|  | Production Example N | 8.2 | 18.5 | 29.4 | 49.2 | 21.5 | 8.3 | 87% | 84% | 113% | 67% | 10% | 10% |
|  | Production Example O | 0.4 | 1.6 | 2.7 | 3.8 | 7.3 | 7.1 | 100% | 85% | 126% | 106% | 57% | 39% |
|  | Formulation Example 3 | −0.1 | −0.1 | 0.1 | 0.2 | 1.1 | 3.1 | 114% | 124% | 121% | 109% | 96% | 59% |
|  | Formulation Example 4 | 23.4 | 45.4 | 49.0 | 44.2 | 16.5 | 10.8 | 77% | 78% | 68% | 47% | 8% | 6% |
| HT1080 | LFA2000 | — | 93.4 | 118.0 | 103.6 | 28.3 | 4.9 | — | 49% | 32% | 15% | 1% | 0% |
|  | Production Example A | 0.1 | 1.4 | 1.8 | 1.8 | 4.3 | 0.4 | 94% | 95% | 91% | 78% | 45% | 38% |
|  | Production Example B | 1.3 | 1.3 | 2.5 | 4.0 | 58.3 | 18.1 | 102% | 103% | 89% | 95% | 33% | 11% |

TABLE 11-continued

| Cells | Formulation Example | β-gal activity (mU/well) Amount of liposomes added (μL/well) | | | | | | Cell survival rate relative to that in liposome-free well Amount of liposomes added (μL/well) | | | | | |
|---|---|---|---|---|---|---|---|---|---|---|---|---|---|
| | | 0.09 | 0.19 | 0.4 | 0.8 | 1.5 | 3.0 | 0.09 | 0.19 | 0.4 | 0.8 | 1.5 | 3.0 |
| | Production Example C | 4.8 | 13.2 | 30.3 | 67.9 | 78.2 | 13.5 | 92% | 78% | 72% | 45% | 29% | 13% |
| | Production Example D | −0.2 | −0.2 | 0.0 | 0.3 | 1.7 | 12.5 | 84% | 70% | 73% | 126% | 52% | 44% |
| | Production Example E | −0.2 | −0.2 | −0.1 | 1.7 | 0.2 | 0.0 | 91% | 69% | 116% | 73% | 40% | 9% |
| | Production Example F | −0.2 | 0.3 | 2.3 | 9.6 | 39.6 | 3.2 | 79% | 68% | 71% | 88% | 19% | 16% |
| | Production Example G | −0.2 | 0.1 | 1.3 | 1.5 | 5.4 | 16.7 | 89% | 70% | 169% | 141% | 55% | 37% |
| | Production Example H | 0.0 | 0.2 | 0.4 | 3.1 | 1.4 | 0.2 | 92% | 191% | 168% | 89% | 39% | 0% |
| | Production Example I | 0.3 | 2.1 | 2.8 | 19.2 | 53.0 | 3.7 | 102% | 77% | 88% | 73% | 32% | 30% |
| | Production Example J | 11.4 | 35.1 | 84.5 | 115.6 | 91.0 | 6.4 | 88% | 74% | 98% | 81% | 20% | 3% |
| | Production Example K | 0.1 | 0.3 | 1.4 | 1.7 | 2.7 | 16.4 | 99% | 78% | 102% | 172% | 78% | 37% |
| | Production Example L | 0.1 | 0.3 | 1.3 | 7.6 | 2.0 | 1.1 | 100% | 74% | 126% | 138% | 44% | 3% |
| | Production Example M | 4.3 | 10.3 | 39.9 | 115.6 | 111.5 | 5.8 | 94% | 72% | 124% | 90% | 20% | 28% |
| | Production Example N | 23.8 | 45.7 | 75.1 | 115.5 | 108.4 | 27.0 | 86% | 51% | 87% | 57% | 13% | 8% |
| | Production Example O | 0.5 | 1.9 | 2.8 | 6.1 | 10.0 | 12.1 | 78% | 61% | 132% | 134% | 51% | 44% |
| | Formulation Example 3 | 1.2 | 2.1 | 2.1 | 4.2 | 14.9 | 28.4 | 102% | 88% | 79% | 74% | 59% | 37% |
| | Formulation Example 4 | 23.9 | 44.7 | 64.6 | 97.9 | 86.7 | 3.0 | 80% | 77% | 60% | 38% | 18% | 1% |

LFA2000: Lipofectamine 2000

TABLE 12

| Cells | Formulation Example | Cytotoxicity score Amount of liposomes added (μL/well) | | | | | | Total protein amount (μg/well) Amount of liposomes added (μL/well) | | | | | |
|---|---|---|---|---|---|---|---|---|---|---|---|---|---|
| | | 0.09 | 0.19 | 0.4 | 0.8 | 1.5 | 3.0 | 0.09 | 0.19 | 0.4 | 0.8 | 1.5 | 3.0 |
| HeLa | LFA2000 | — | 1.8 | 2.5 | 3.3 | 4.0 | 5.0 | — | 8.7 | 6.6 | 3.9 | 2.0 | 1.0 |
| | Production Example A | 0.0 | 0.0 | 0.0 | 1.0 | 3.0 | 2.5 | 11.4 | 12.9 | 11.0 | 11.7 | 4.6 | 6.9 |
| | Production Example B | 0.0 | 0.5 | 1.0 | 1.0 | 4.0 | 4.0 | 10.9 | 11.8 | 11.0 | 10.2 | 2.0 | 1.6 |
| | Production Example C | 0.5 | 1.5 | 2.5 | 3.5 | 4.0 | 5.0 | 11.4 | 11.2 | 9.4 | 5.3 | 2.4 | 1.5 |
| | Production Example D | 0.0 | 0.0 | 0.5 | 1.0 | 1.5 | 3.0 | 10.7 | 12.5 | 12.2 | 11.4 | 11.6 | 5.3 |
| | Production Example E | 0.0 | 0.0 | 0.0 | 0.0 | 1.0 | 3.0 | 11.2 | 11.6 | 12.6 | 11.2 | 10.7 | 4.6 |
| | Production Example F | 0.0 | 0.5 | 1.0 | 2.5 | 5.0 | 4.0 | 11.6 | 12.5 | 12.9 | 7.6 | 3.4 | 1.9 |
| | Production Example G | 0.0 | 0.0 | 1.0 | 2.0 | 3.0 | 4.0 | 10.6 | 10.9 | 10.9 | — | 7.7 | 3.6 |
| | Production Example H | 0.0 | 0.0 | 0.0 | 0.5 | 1.0 | 4.0 | 10.2 | 11.5 | 10.8 | 9.9 | 9.2 | 3.5 |
| | Production Example I | 0.0 | 0.0 | 0.0 | 2.0 | 3.0 | 4.0 | 12.0 | 12.3 | 12.0 | 10.2 | 5.6 | 3.2 |
| | Production Example J | 0.5 | 1.0 | 2.0 | 3.0 | 4.0 | 5.0 | 11.8 | 12.0 | 9.6 | 4.7 | 2.1 | 1.5 |
| | Production Example K | 0.0 | 0.0 | 0.5 | 1.0 | 2.0 | 4.0 | 11.8 | 11.9 | 11.5 | 11.0 | 10.9 | 3.8 |
| | Production Example L | 0.0 | 0.0 | 0.0 | 0.5 | 2.0 | 4.0 | 12.5 | 12.3 | 11.6 | 11.1 | 9.6 | 3.8 |
| | Production Example M | 0.0 | 1.0 | 2.0 | 3.0 | 4.0 | 4.0 | 11.5 | 10.8 | 10.0 | 5.8 | 2.1 | 3.4 |
| | Production Example N | 0.5 | 0.5 | 1.0 | 3.0 | 4.0 | 5.0 | 12.2 | 12.6 | 11.4 | 7.6 | 3.0 | 2.3 |
| | Production Example O | 0.0 | 0.0 | 1.0 | 2.5 | 3.0 | 3.5 | 11.7 | 11.7 | 11.1 | 11.3 | 9.6 | 6.3 |
| | Formulation | 0.0 | 0.0 | 0.0 | 0.0 | 0.5 | 3.0 | 12.2 | 12.8 | 11.8 | 11.6 | 12.1 | 8.0 |

TABLE 12-continued

| Cells | Formulation Example | Cytotoxicity score Amount of liposomes added (μL/well) | | | | | | Total protein amount (μg/well) Amount of liposomes added (μL/well) | | | | | |
|---|---|---|---|---|---|---|---|---|---|---|---|---|---|
| | | 0.09 | 0.19 | 0.4 | 0.8 | 1.5 | 3.0 | 0.09 | 0.19 | 0.4 | 0.8 | 1.5 | 3.0 |
| | Example 3 Formulation Example 4 | 0.5 | 1.0 | 2.5 | 3.0 | 4.0 | 4.0 | 11.2 | 11.2 | 10.0 | 6.1 | 2.1 | 2.2 |
| HT1080 | LFA2000 | — | 2.3 | 3.0 | 4.0 | 5.0 | 5.0 | — | 8.0 | 6.6 | 3.7 | 1.1 | 0.8 |
| | Production Example A | 0.0 | 0.0 | 0.0 | 0.0 | 0.0 | 0.5 | 10.6 | 10.2 | 10.6 | 10.2 | 9.4 | 9.3 |
| | Production Example B | 0.0 | 0.0 | 0.0 | 0.0 | 1.5 | 4.0 | 10.2 | 10.1 | 9.7 | 9.6 | 8.2 | 2.6 |
| | Production Example C | 0.0 | 0.0 | 0.0 | 1.0 | 2.0 | 4.0 | 9.4 | 9.9 | 9.4 | 8.0 | 7.4 | 3.3 |
| | Production Example D | 0.0 | 0.0 | 0.0 | 0.0 | 0.0 | 0.0 | 9.4 | 9.9 | 9.7 | 9.2 | 10.3 | 9.4 |
| | Production Example E | 0.0 | 0.0 | 0.0 | 0.0 | 0.0 | 5.0 | 9.5 | 10.0 | 9.5 | 8.9 | 8.8 | 2.0 |
| | Production Example F | 0.0 | 0.0 | 0.0 | 0.0 | 1.5 | 2.5 | 9.8 | 10.4 | 9.7 | 9.0 | 6.3 | 4.8 |
| | Production Example G | 0.0 | 0.0 | 0.0 | 0.5 | 0.5 | 1.0 | 9.4 | 10.0 | 10.3 | 9.0 | 9.4 | 7.5 |
| | Production Example H | 0.0 | 0.0 | 0.0 | 0.0 | 0.0 | 5.0 | 10.6 | 10.4 | 10.0 | 9.4 | 9.3 | 0.8 |
| | Production Example I | 0.0 | 0.0 | 0.0 | 0.0 | 1.5 | 2.5 | 8.9 | 8.8 | 9.1 | 8.4 | 6.6 | 6.5 |
| | Production Example J | 0.0 | 0.0 | 0.0 | 1.0 | 3.0 | 5.0 | 8.2 | 7.1 | 7.0 | 5.9 | 4.3 | 1.9 |
| | Production Example K | 0.0 | 0.0 | 0.0 | 0.0 | 0.5 | 3.0 | 9.3 | 8.5 | 8.7 | 8.8 | 8.8 | 6.9 |
| | Production Example L | 0.0 | 0.0 | 0.0 | 0.5 | 2.0 | 5.0 | 8.4 | 8.6 | 8.7 | 8.1 | 7.9 | 2.0 |
| | Production Example M | 0.0 | 0.0 | 0.5 | 2.0 | 3.0 | 3.5 | 8.8 | 8.8 | 8.6 | 6.7 | 5.0 | 5.1 |
| | Production Example N | 0.0 | 0.0 | 1.0 | 2.0 | 3.0 | 4.0 | 8.5 | 8.6 | 7.8 | 6.1 | 4.9 | 3.4 |
| | Production Example O | 0.0 | 0.0 | 0.0 | 0.0 | 1.0 | 2.0 | 9.2 | 8.8 | 8.9 | 8.2 | 8.7 | 7.5 |
| | Formulation Example 3 | 0.0 | 0.0 | 0.0 | 0.0 | 0.5 | 1.5 | 8.9 | 9.3 | 8.5 | 9.8 | 8.6 | 6.9 |
| | Formulation Example 4 | 0.0 | 0.0 | 0.0 | 1.0 | 4.0 | 5.0 | 10.3 | 9.8 | 9.5 | 8.0 | 5.0 | 1.0 |

LFA2000: Lipofectamine 2000

As shown in Tables 11 and 12, among the nucleic-acid-transfecting compositions of the present invention, particularly, the compositions of Production Examples C, J, and N and Formulation Example 4 exhibited excellent performance.

Test Example 7

Test for Transfection of Nucleic Acid into HeLa Cells

Each of the enhancers shown in Table 13 was diluted with a DMEM medium to different concentrations so that the amount of the enhancer finally added to cells was "Enhancer amount (μg/well)" shown in Table 13. Separately, the lyophilized liposome product of Formulation Example 4 was reconstituted in a manner similar to that described in Test Example 5 and then diluted with a DMEM medium so that the amount of the liposomes finally added to cells was "Amount of liposomes added (μL/well)" shown in Table 13. The thus-diluted liposome solution was added to an equiamount of the above-diluted enhancer, followed by incubation at room temperature for 20 minutes. After regulation of the volume of the mixture with a DMEM medium, in a manner similar to that described in Test Example 5, a DNA/liposome complex was formed, and transfection was carried out. Subsequently, cytotoxicity was evaluated according to the aforementioned scores, and determination of β-gal activity, quantitative determination of protein, and viable cell counting were carried out. Lipofectamine 2000 was also tested in a manner similar to that described in Test Example 5. The results are shown in Table 13.

TABLE 13

| | HeLa cells Amount of liposomes added (μL/well) | | | | | | | |
|---|---|---|---|---|---|---|---|---|
| | 0.38 | 0.75 | 0.38 | 0.75 | 0.38 | 0.75 | 0.38 | 0.75 |
| | β-gal activity (mU/well) | | Cell survival rate | | Cytotoxicity score | | Total protein (μg/well) | |
| LFA2000 only | 18.1 | 40.4 | 65% | 40% | 2.0 | 3.0 | 7.1 | 4.2 |
| Formulation Example 4 only | 20.0 | 30.8 | 61% | 53% | 1.5 | 3.0 | 8.2 | 5.1 |

TABLE 13-continued

| | | HeLa cells Amount of liposomes added (μL/well) | | | | | | | |
|---|---|---|---|---|---|---|---|---|---|
| | | 0.38 | 0.75 | 0.38 | 0.75 | 0.38 | 0.75 | 0.38 | 0.75 |
| | | β-gal activity (mU/well) | | Cell survival rate | | Cytotoxicity score | | Total protein (μg/well) | |
| Enhancer | Enhancer amount (μg/well) | | | | | | | | |
| Sodium butyrate | 2.5 | 20.4 | — | 67% | — | 1.5 | — | 8.8 | — |
| | 5 | 19.8 | — | 73% | — | 1.0 | — | 7.1 | — |
| | 10 | 18.7 | — | 65% | — | 1.0 | — | 7.6 | — |
| | 20 | 20.9 | — | 66% | — | 1.5 | — | 7.8 | — |
| | 40 | 26.7 | — | 68% | — | 2.0 | — | 7.8 | — |
| Poly L-lysine | 0.625 | 23.9 | 54.1 | 62% | 73% | 0.5 | 1.0 | 8.6 | 7.2 |
| | 1.25 | 3.4 | 6.6 | 71% | 94% | 0.0 | 0.5 | 9.3 | 8.5 |
| | 2.5 | 0.6 | 1.5 | 70% | 99% | 0.0 | 0.0 | 9.7 | 8.9 |
| | 5 | 0.6 | 0.7 | 70% | 97% | 0.5 | 0.0 | 9.5 | 8.8 |
| | 10 | 0.1 | 0.2 | 76% | 99% | 0.5 | 0.5 | 9.2 | 8.2 |
| Protamine | 0.625 | 30.4 | 46.2 | 52% | 53% | 1.5 | 3.0 | 7.8 | 5.5 |
| | 1.25 | 9.8 | 26.3 | 59% | 75% | 0.5 | 1.0 | 9.3 | 7.6 |
| | 2.5 | 4.8 | 10.1 | 64% | 78% | 0.5 | 0.5 | 9.9 | 8.8 |
| | 5 | 0.9 | 3.1 | 69% | 91% | 0.5 | 0.5 | 10.2 | 8.9 |
| | 10 | 0.1 | 0.5 | 70% | 95% | 0.5 | 0.5 | 10.3 | 9.1 |
| Pronectin | 0.00625 | 23.3 | 28.7 | 41% | 40% | 2.0 | 4.0 | 7.1 | 4.8 |
| | 0.0125 | 19.4 | 25.1 | 43% | 41% | 2.0 | 3.5 | 7.6 | 4.1 |
| | 0.025 | 15.5 | 16.2 | 44% | 30% | 2.0 | 3.5 | 7.6 | 4.0 |
| | 0.05 | 3.2 | 6.2 | 53% | 40% | 1.5 | 3.0 | 8.3 | 4.7 |
| | 0.1 | 0.8 | 2.3 | 46% | 52% | 2.0 | 3.0 | 8.8 | 5.0 |
| Spermine | 6.25 | 0.8 | 1.8 | 3% | 4% | 0.0 | 4.0 | 3.9 | 1.6 |
| | 12.5 | 1.0 | 0.1 | 6% | 3% | 0.0 | 4.0 | 4.9 | 1.5 |
| | 25 | 0.2 | 0.0 | 3% | 12% | 0.0 | 4.0 | 5.4 | 1.6 |
| | 50 | 0.2 | 0.1 | 17% | 50% | 2.0 | 4.0 | 7.1 | 3.1 |
| | 100 | 0.1 | 0.3 | 51% | 68% | 2.0 | 2.0 | 5.8 | 4.8 |

LFA2000: Lipofectamine 2000

Test Example 8

Test for Transfection of Nucleic Acid into HT1080 Cells

The procedure of Test Example 7 was repeated, except that HeLa cells were replaced with HT1080 cells. In a manner similar to that described in Test Example 7, cytotoxicity was evaluated according to the aforementioned scores, and determination of β-gal activity, quantitative determination of protein, and viable cell counting were carried out. The results are shown in Table 14.

TABLE 14

| | | HT1080 cells Amount of liposomes added (μL/well) | | | | | | | |
|---|---|---|---|---|---|---|---|---|---|
| | | 0.38 | 0.75 | 0.38 | 0.75 | 0.38 | 0.75 | 0.38 | 0.75 |
| | | β-gal activity (mU/well) | | Cell survival rate | | Cytotoxicity score | | Total protein (μg/well) | |
| LFA2000 only | | 26.6 | 46.6 | 55% | 34% | 2.0 | 3.3 | 7.6 | 5.7 |
| Formulation Example 4 only | | 34.4 | 89.1 | 39% | 31% | 1.5 | 2.5 | 9.4 | 7.4 |
| Enhancer | Enhancer amount (μg/well) | | | | | | | | |
| Sodium butyrate | 2.5 | 45.0 | — | 55% | — | 1.5 | — | 8.5 | — |
| | 5 | 40.2 | — | 50% | — | 1.5 | — | 9.4 | — |
| | 10 | 37.3 | — | 53% | — | 2.0 | — | 8.1 | — |
| | 20 | 40.3 | — | 52% | — | 2.5 | — | 9.2 | — |
| | 40 | 45.6 | — | 62% | — | 3.0 | — | 9.1 | — |
| Poly L-lysine | 0.625 | 76.7 | 98.0 | 53% | 62% | 2.0 | 2.5 | 9.1 | 8.4 |
| | 1.25 | 49.5 | 93.8 | 72% | 75% | 2.0 | 2.0 | 10.3 | 9.6 |
| | 2.5 | 25.7 | 59.2 | 78% | 82% | 1.0 | 1.5 | 10.5 | 10.0 |
| | 5 | 12.2 | 42.7 | 65% | 86% | 0.5 | 0.5 | 10.8 | 10.0 |
| | 10 | 8.8 | 25.3 | 80% | 82% | 1.0 | 1.0 | 10.4 | 10.0 |
| Protamine | 0.625 | 79.3 | 103.9 | 46% | 39% | 1.5 | 2.5 | 9.4 | 7.6 |
| | 1.25 | 61.5 | 103.9 | 73% | 50% | 1.5 | 2.0 | 10.7 | 8.8 |
| | 2.5 | 23.1 | 49.8 | 78% | 76% | 1.0 | 2.0 | 10.3 | 9.0 |

TABLE 14-continued

|  |  | HT1080 cells Amount of liposomes added (μL/well) | | | | | | | |
|---|---|---|---|---|---|---|---|---|---|
|  |  | 0.38 | 0.75 | 0.38 | 0.75 | 0.38 | 0.75 | 0.38 | 0.75 |
|  |  | β-gal activity (mU/well) | | Cell survival rate | | Cytotoxicity score | | Total protein (μg/well) | |
|  | 5 | 4.1 | 19.5 | 71% | 81% | 0.5 | 2.0 | 11.5 | 9.2 |
|  | 10 | 2.7 | 15.1 | 83% | 89% | 0.5 | 1.0 | 10.9 | 9.2 |
| Pronectin | 0.00625 | 87.2 | 102.6 | 33% | 25% | 1.5 | 3.0 | 9.7 | 6.5 |
|  | 0.0125 | 70.2 | 107.3 | 45% | 33% | 1.0 | 3.0 | 9.6 | 7.3 |
|  | 0.025 | 52.0 | 92.1 | 41% | 33% | 0.5 | 2.5 | 9.7 | 7.3 |
|  | 0.05 | 3.3 | 16.0 | 57% | 51% | 1.0 | 2.5 | 11.5 | 8.0 |
|  | 0.1 | 0.3 | 4.4 | 85% | 69% | 1.0 | 2.0 | 10.3 | 9.3 |
| Spermine | 6.25 | 31.1 | 76.5 | 80% | 78% | 2.5 | 2.0 | 9.7 | 7.7 |
|  | 12.5 | 29.1 | 64.6 | 101% | 82% | 2.0 | 2.5 | 9.4 | 7.4 |
|  | 25 | 34.9 | 72.9 | 104% | 101% | 2.5 | 3.0 | 10.0 | 7.6 |
|  | 50 | 21.5 | 10.9 | 110% | 165% | 2.0 | 2.0 | 10.1 | 8.7 |
|  | 100 | 6.8 | 1.3 | 144% | 203% | 1.0 | 2.0 | 9.4 | 9.1 |

LFA2000: Lipofectamine 2000

As shown in Tables 13 and 14, when an appropriate amount of an enhancer was added to the liposome solution, the resultant composition exhibited excellent nucleic-acid-transfecting performance and low cytotoxicity. Particularly, sodium butyrate, poly L-lysine, protamine, and pronectin (in particular, poly L-lysine and protamine) were found to exhibit excellent effects.

Test Example 9

Test for Transfection of Nucleic Acid into HeLa, HT1080, 293T, COS-1, and NB1RGB Cells There were prepared compositions by incorporating protamine into the lyophilized liposome product of Production Example J at different concentrations. Specifically, an aqueous protamine sulfate solution having a protamine concentration of twice that shown in Table 15 was prepared. Separately, the lyophilized liposome product of Production Example J was reconstituted with an appropriate amount of water for injection to give a liposome dispersion having a DC-1-14 concentration of about 2 mM. The aqueous protamine sulfate solution was added to an equiamount of the liposome dispersion. By use of the resultant dispersion, a test for a nucleic acid transfection into cells (i.e., HeLa, HT1080, 293T, COS-1, or NB1RGB cells) was carried out in a manner similar to that described in Test Example 5, and β-gal activity was determined. The results are shown in Table 15.

TABLE 15

|  |  | β-gal activity (mU/well) | | | | | | | | | |
|---|---|---|---|---|---|---|---|---|---|---|---|
|  |  | HeLa cells | | HT1080 cells | | 293T cells | | COS-1 cells | | NB1RGB cells | |
| DNA amount | Amount of protamine added to liposome | Amount of liposome dispersion added (/well) | | | | | | | | | |
| (/well) | dispersion (mg/mL) | 0.38 μL | 0.75 μL | 0.38 μL | 0.75 μL | 0.38 μL | 0.75 μL | 0.38 μL | 0.75 μL | 0.38 μL | 0.75 μL |
| 100 ng DNA | LFA2000 | 48 | 112 | 48 | 157 | 349 | 1026 | 39 | 192 | 4.2 | 12.5 |
|  | 0 | 36 | 26 | 286 | 367 | 496 | 647 | 185 | 300 | 1.3 | 1.6 |
|  | 0.2 | 61 | 66 | 569 | 559 | 657 | 554 | 280 | 186 | 8.1 | 4.2 |
|  | 0.4 | 109 | 92 | 551 | 450 | 629 | 686 | 131 | 152 | 9.6 | 5.3 |
|  | 0.6 | 257 | 144 | 472 | 491 | 610 | 709 | 82 | 131 | 4.6 | 5.6 |
|  | 0.8 | 256 | 160 | 298 | 456 | 571 | 827 | 73 | 153 | 5 | 3 |
|  | 1 | 252 | 190 | 212 | 388 | 631 | 625 | 53 | 140 | 3.4 | 2.6 |
|  | 1.2 | 223 | 195 | 206 | 400 | 489 | 530 | 61 | 90 | 2.3 | 1.9 |
|  | 1.5 | 145 | 87 | 161 | 221 | 532 | 598 | 49 | 63 | 1.7 | 1.4 |
| 200 ng DNA | LFA2000 | 93 | 205 | 186 | 267 | 394 | 750 | 136 | 458 | 3.9 | — |
|  | 0 | 21 | 43 | 242 | 339 | 306 | 563 | 165 | 265 | — | — |
|  | 0.2 | 15 | 74 | 236 | 299 | 287 | 470 | 100 | 228 | — | — |
|  | 0.4 | 21 | 77 | 173 | 398 | 431 | 599 | 69 | 438 | 19.4 | — |
|  | 0.6 | 81 | 152 | 226 | 500 | 481 | 872 | 165 | 318 | 26.3 | — |
|  | 0.8 | 155 | 162 | 635 | 592 | 947 | 763 | 369 | 311 | 21 | 15 |
|  | 1 | 256 | 180 | 690 | 622 | 870 | 837 | 257 | 301 | 26.6 | 10.6 |
|  | 1.2 | 294 | 238 | 591 | 563 | 667 | 806 | 193 | 279 | 24.7 | 7.5 |
|  | 1.5 | 262 | 263 | 475 | 520 | 436 | 727 | 146 | 306 | 13.1 | 0.0 |

The liposome dispersion prepared by incorporating protamine (about 0.6 to about 1.0 mg/mL) into the lyophilized liposome product of Production Example J (1 mM) exhibited excellent nucleic-acid-transfecting performance in most of the aforementioned types of cells.

INDUSTRIAL APPLICABILITY

The composition of the present invention exhibits low cytotoxicity and realizes an effective nucleic acid transfection into cells. Therefore, the composition is useful as a nucleic-acid-transfecting agent (e.g., a nucleic-acid-transfecting reagent or drug).

3. The composition of claim 1 wherein the nucleic acid is a gene.

4. The composition of claim 1 wherein the nucleic acid is a DNA oligonucleotide, an RNA oligonucleotide, antisense DNA, antisense RNA, shRNA, siRNA, or miRNA.

5. The composition of claim 1 that further comprises a bioactive substance.

6. The composition of claim 1 that is in the form of a lipid membrane structure.

7. The composition of claim 1 that is in the form of a liposome.

8. The composition of claim 1 that is lyophilized.

The invention claimed is:

1. A composition in a form suitable for transfecting a nucleic acid into a cell comprising ditetradecyldimethylammonium bromide, dioleoylphosphatidylethanolamine, cholesterol, and a nucleic acid, with a cation/anion charge ratio of 1:1 to 1:6.

2. The composition of claim 1, further comprising protamine.

9. A method for introducing or transfecting a nucleic acid into a cell, comprising contacting in vitro or in vivo a cell with the composition of claim 1.

10. The composition of claim 1, wherein the ratio of the ditetradecyldimethylammonium bromide to the dioleoylphosphatidylethanolamine is 1:4 to 4:1.

11. The composition of claim 1, which contains up to 50 mol % of the cholesterol based on the total lipid content of the composition.

12. The composition of claim 10, which contains up to 50 mol % of the cholesterol based on the total lipid content of the composition.

* * * * *

```
                           SEQUENCE LISTING

<160> NUMBER OF SEQ ID NOS: 4

<210> SEQ ID NO 1
<211> LENGTH: 27
<212> TYPE: RNA
<213> ORGANISM: Artificial sequence
<220> FEATURE:
<223> OTHER INFORMATION: siRNA(sense sequence)

<400> SEQUENCE: 1
acaucacgua cgcggaauac uucgaag                                         27

<210> SEQ ID NO 2
<211> LENGTH: 27
<212> TYPE: RNA
<213> ORGANISM: Artificial sequence
<220> FEATURE:
<223> OTHER INFORMATION: siRNA(antisense sequence)

<400> SEQUENCE: 2
uauguagugc augcgccuua ugaagcu                                         27

<210> SEQ ID NO 3
<211> LENGTH: 27
<212> TYPE: RNA
<213> ORGANISM: Artificial sequence
<220> FEATURE:
<223> OTHER INFORMATION: siRNA(sense sequence)

<400> SEQUENCE: 3
acaucacuua cgcugaguac uucgaag                                         27

<210> SEQ ID NO 4
<211> LENGTH: 27
<212> TYPE: RNA
<213> ORGANISM: Artificial sequence
<220> FEATURE:
<223> OTHER INFORMATION: siRNA(antisense sequence)

<400> SEQUENCE: 4
uauguaguga augcgacuca ugaagcu                                         27
```